United States Patent [19]

Duthaler et al.

[11] Patent Number: 4,855,084

[45] Date of Patent: Aug. 8, 1989

[54] ANTHRAQUINOYLCARBOXYLIC ACID HYDRAZIDES, CURABLE COMPOSITIONS AND USE THEREOF

[75] Inventors: Rudolf Duthaler, Bettingen, Switzerland; Jürgen Finter, Freiburg, Fed. Rep. of Germany; Walter Fischer, Reinach; Visvanathan Ramanathan, Basel, both of Switzerland

[73] Assignee: Ciba-Geigy Corporation, Ardsley, N.Y.

[21] Appl. No.: 208,522

[22] Filed: Jun. 20, 1988

[30] Foreign Application Priority Data

Jul. 1, 1987 [CH] Switzerland ............... 2484/87

[51] Int. Cl.[4] ................. C07C 103/75; C09B 1/00
[52] U.S. Cl. ........................................... 260/377
[58] Field of Search ................................. 260/377

[56] References Cited

U.S. PATENT DOCUMENTS

| | | | |
|---|---|---|---|
| 2,884,424 | 4/1959 | Klingsberg | 260/308 |
| 4,285,874 | 8/1981 | Braden et al. | 260/377 |
| 4,381,261 | 4/1983 | Bonnet | 260/377 |
| 4,420,627 | 12/1983 | Widiger | 260/377 |
| 4,426,328 | 1/1984 | Adam et al. | 260/377 |
| 4,510,279 | 4/1985 | Kishimura et al. | 524/144 |
| 4,657,842 | 4/1987 | Finter et al. | 430/280 |

FOREIGN PATENT DOCUMENTS 55-89245 7/1980 Japan.

*Primary Examiner*—Glennon H. Hollrah
*Assistant Examiner*—Raymond Covington
*Attorney, Agent, or Firm*—Stephen V. O'Brien; Luther A. R. Hall

[57] ABSTRACT

Anthraquinones of formula I

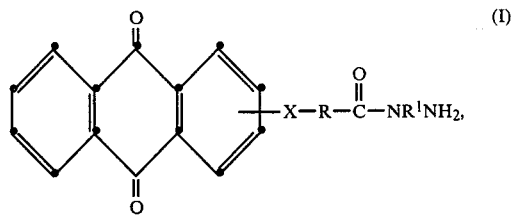

wherein X is the group $-CR^2R^3-$, where $R^2$ is H, $-CN$ or $C_1-C_5$-alkyl and $R^3$ is H or $-CN$, $R^1$ is H or $C_1-C_5$-alkyl and R is a direct bond or linear or branched $C_1-C_{18}$-alkylene which, alone or together with the $-CR^2R^3-$ group, can be interrupted by one or more $-O-$ when $R^2$ and/or $R^3$ are not $-CN$, and curable compositions comprising (a) an epoxy resin, (b) a hardener if necessary, (c) an anthraquinone of formula I and (d) an amino alcohol. The cured compositions are photosensitive and are suitable for the preparation of coatings and metallic images by electroless metal deposition.

6 Claims, No Drawings

ANTHRAQUINOYLCARBOXYLIC ACID HYDRAZIDES, CURABLE COMPOSITIONS AND USE THEREOF

The invention relates to anthraquinoylcarboxylic acid hydrazides, to a curable composition consisting of (a) an epoxy resin, (b) a hardener if necessary, (c) an anthraquinonecarboxylic acid hydrazide and (d) an amino alcohol, and to the use thereof for the preparation of metallic coatings or images.

European patent application A-0 112 798 proposes photosensitive crosslinked reaction products based on epoxy resins. With the concomitant use of metal salts of groups Ib and VIII of the periodic table of the elements, metal nuclei can be produced by exposure to light and these can be increased by electroless metal deposition. It is desirable to produce metallic coatings or images, by electroless metal deposition, direct on photosensitive epoxy resins without the concomitant use of metal salts.

The invention relates to anthraquinones of formula I

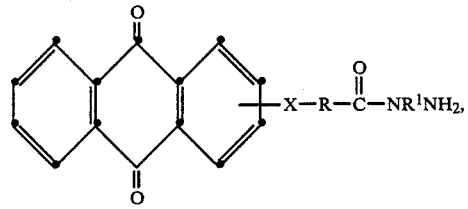

wherein X is the group $-CR^2R^3-$, where $R^2$ is H, $-CN$ or $C_1-C_5$-alkyl and $R^3$ is H or $-CN$, $R^1$ is H or $C_1-C_5$-alkyl and R is a direct bond or linear or branched $C_1-C_{18}$-alkylene which, alone or together with the $-CR^2R^3-$ group, can be interrupted by one or more $-O-$ when $R^2$ and/or $R^3$ are not $-CN$.

The group

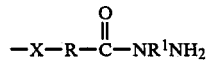

is preferably bonded in the 2-position of the anthraquinone.

In a preferred embodiment of the invention, the anthraquinones of formula I are those wherein X is the group $-CR^2R^3-$ in which $R^2$ is H or $C_1-C_5$-alkyl and $R^3$ is H. Those in which $R^2$ and $R^3$ are both H are especially preferred.

$R^1$ and $R^2$ can be linear or branched alkyl; alkyl is preferably e.g. methyl or ethyl. $R^1$ is preferably H or methyl. R as alkylene may be branched or, preferably, linear. It preferably contains 1 to 12, especially 1 to 8, C atoms.

In another preferred embodiment of the invention, X is $-CH_2-$ and R is a direct bond or a linear alkylene having 1 to 8 C atoms.

R as alkylene may be interrupted by $-O-$, preferably by 1 to 4, especially 1 or 2, $-O-$. In a preferred embodiment of the invention, the alkylene interrupted by $-O-$ has the formula $-(C_mH_{2m}-O)_y-$, wherein m is a number from 2 to 4, preferably 2 or 3 and especially 2, and y is a number from 1 to 6, preferably 1-4 and especially 1 or 2.

According to U.S. Pat. No. 2,884,424, anthraquinon-2-carboxylic acid hydrazide can only be prepared by reacting an appropriate ester with an excess of hydrazine to give the leuco form and then oxidizing the latter. It has been found, surprisingly, that the anthraquinones of the invention are formed direct when alcoholic solutions of the appropriate esters are reacted with hydrazine.

The invention further relates to a process for the preparation of anthraquinones of formula I, wherein an anthraquinonecarboxylic acid ester of formula II

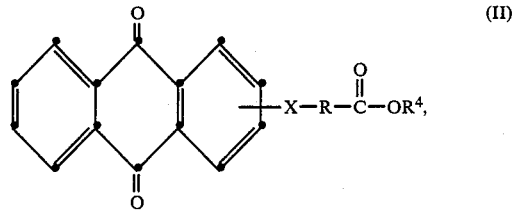

wherein X and R are as defined above or the group $-XR-$ is a direct bond and $R^4O-$ is the radical of an alcohol, is reacted in the presence of an alcohol with a hydrazine of formula III

wherein $R^1$ is as defined above, or with the hydrate or salts thereof.

$R^4$ in formula II is preferably $C_1-C_6$-alkyl and especially $C_1-C_4$-alkyl. $R^4$ is, in particular, methyl or ethyl.

The alcohol is preferably an alkanol having, in particular, 1-4 C atoms. It is preferred to use alkanols whose alkyl radical is identical with $R^4$. The use of ethanol is especially preferred.

The reaction is advantageously carried out under an inert gas atmosphere. The reaction temperature can be 30° to 180° C. and is preferably 50° to 120° C.

The alkanol can serve as solvent. Other inert solvents can additionally be used, e.g. ethers (diethyl ether, dioxane, tetrahydrofuran), cellosolve, sulfoxides and sulfones, and N-alkylated acid amides.

The hydrazines of formula III are known. Hydrazine hydrate is advantageously used. Salts can be derived e.g. from mineral or carboxylic acids.

The esters of formula II are known or can be prepared by processes known per se. Japanese patent disclosure Sho 55/89245 proposes the preparation of (anthraquino-2-yl)acetic acid esters by the substitution of anthraquinoyl chloride with malonic acid diesters. Malonitrile and malonic ester-nitriles can be used analogously. The anthraquinoylmalonic derivatives obtainable in this way can be reacted in known manner with $C_1-C_5$-alkyl halides or with carbalkoxyalkyl halides. Partial hydrolysis of the nitrile or ester groups and, in some cases, decarboxylation gives further esters of formula II after esterification. These reactions can also be carried out with the known anthraquinoylacetonitrile.

The esters of formula II can also be obtained by the known reaction of anthracene with alkenecarboxylic acid esters and subsequent oxidation e.g. with Jones reagent. A further possibility is a stepwise synthesis involving the reaction of phenalkylcarboxylic acid esters, known per se, with phthalic anhydride, subsequent cyclization to the anthraquinonealkanecarboxylic acid and esterification thereof. Phenalkylcarboxylic acid esters can also be obtained by the catalytic hydrogenation of benzoylalkanecarboxylic acids and simultaneous or subsequent esterification.

Esters of formula II wherein R is alkylene interrupted by —O— can be prepared by first reacting a halogenoalkylanthraquinone with an alkylenediol and then, in some cases, with alkylene oxides. The hydroxyl compounds obtained can then be reacted with alkenecarboxylic acid esters or halogenoalkylcarboxylic acid esters.

The compounds of formula I are suitable for the preparation of photosensitive cured epoxy resins. The invention further relates to a curable composition comprising
(a) at least one epoxy resin with an average of more than one epoxy group in the molecule,
(b) an epoxy resin hardener if necessary,
(c) at least one anthraquinone of formula I, the group —XR— additionally being a direct bond, and
(d) at least one primary or secondary aliphatic amine containing at least one hydroxyl group in the aliphatic radical.

The preferences mentioned previously apply to the compounds of formula I.

The epoxy resin preferably contains an average of at least 2 epoxy groups in the molecule.

Possible epoxy resins are, in particular, those with an average of more than one glycidyl group, β-methylglycidyl group or 2,3-epoxycyclopentyl group bonded to a heteroatom (e.g. sulfur, preferably oxygen or nitrogen); these are, in particular, bis(2,3-epoxycyclopentyl)ether; diglycidyl or polyglycidyl ethers of polyhydric aliphatic alcohols such as butane-1,4-diol, or polyalkylene glycols such as polypropylene glycols; diglycidyl or polyglycidyl ethers of cycloaliphatic polyols such as 2,2-bis(4-hydroxycyclohexyl)propane; diglycidyl or polyglycidyl ethers of polyhydric phenols such as resorcinol, bis(p-hydroxyphenyl)methane, 2,2-bis(p-hydroxyphenyl)propane (=diomethane), 2,2-bis(4'-hydroxy-3',5'-dibromophenyl)propane and 1,1,2,2-tetrakis(p-hydroxyphenyl)ethane, or of condensation products of phenols with formaldehyde which are obtained under acid conditions, such as phenol novolaks and cresol novolaks; di(β-methylglycidyl) or poly(β-methylglycidyl) ethers of the abovementioned polyhydric alcohols or polyhydric phenols; polyglycidyl esters of polybasic carboxylic acids such as phthalic acid, terephthalic acid, $\Delta^4$-tetrahydrophthalic acid and hexahydrophthalic acid; N-glycidyl derivatives of amines, amides and heterocyclic nitrogen bases, such as N,N-diglycidylaniline, N,N-diglycidyltoluidine, N,N,O-triglycidyl-p-aminophenol and N,N,N',N'-tetraglycidyl-bis(p-aminophenyl)methane; triglycidyl isocyanurate; N,N'-diglycidylethyleneurea; N,N'-diglycidyl-5,5-dimethylhydantoin, N,N'-diglycidyl-5-isopropylhydantoin, N,N-methylene-bis(N',N'-diglycidyl)-5,5-dimethylhydantoin and 1,3-bis(N-glycidyl-5,5-dimethylhydantoin)-2-glycidyloxypropane; and N,N'-diglycidyl-5,5-dimethyl-6-isopropyl-5,6-dihydrouracil.

Glycidylated novolaks, hydantoins, aminophenols, bisphenols or aromatic diamines are a preferred group of epoxy resins. Especially preferred compositions contain, as epoxy resin, a glycidylated cresol novolak, bisphenol A diglycidyl ether, bisphenol A diglycidyl ether "advanced" with bisphenol A, hydantoin N,N'-bisglycide, 2-hydroxypropylene-1,3-bishydantoin triglycide, p-aminophenol triglycide, diaminodiphenylmethane tetraglycide or mixtures thereof.

Prereacted adducts of such epoxides with epoxy hardeners are also suitable, e.g. the above-mentioned adduct of bisphenol A diglycidyl ether and bisphenol A.

Possible epoxy resin hardeners are acidic or basic compounds. Examples of suitable hardeners are: amines such as aliphatic, cycloaliphatic or aromatic, primary, secondary and tertiary amines, e.g. ethylenediamine, hexamethylenediamine, trimethylhexamethylenediamine, diethylenetriamine, triethylenetetramine, tetraethylenepentamine, N,N-dimethylpropylene-1,3-diamine, N,N-diethylpropylene-1,3-diamine, 2,2-bis(4'-aminocyclohexyl)propane, 3,5,5-trimethyl-3-(aminoethyl)-cyclohexylamine ("isophoronediamine") and Mannich bases such as 2,4,6-tris(dimethylaminomethyl)phenol; m-phenylenediamine, p-phenylenediamine, bis(4-aminophenyl)methane, bis(4-aminophenyl)sulfone and m-xylylenediamine; adducts of acrylonitrile or monoepoxides, e.g. ethylene oxide or propylene oxide, and polyalkylenepolyamines, e.g. diethylenetriamine or triethylenetetramine; adducts of an excess of polyamines, e.g. diethylenetriamine or triethylenetetramine, and polyepoxides, e.g. diomethane polyglycidyl ethers; adducts of monophenols or polyphenols and polyamides; polyamides, in particular those derived from aliphatic polyamines, e.g. diethylenetriamine or triethylenetetramine, and dimerized or trimerized unsaturated fatty acids, e.g. dimerized linoleic acid (VERSAMID$^R$); polysulfides (THIOKOL$^R$); aniline-formaldehydes; polyhydric phenols, e.g. resorcinol, 2,2-bis(4-hydroxyphenyl)propane or phenolformaldehyde resins; polybasic carboxylic acids and their anhydrides, e.g. phthalic anhydride, $\Delta^4$-tetrahydrophthalic anhydride, hexahydrophthalic anhydride, 4-methylhexahydrophthalic anhydride, 3,6-endomethylene-$\Delta^4$-tetrahydrophthalic anhydride, 4-methyl-3,6-endomethylene-$\Delta^4$-tetrahydrophthalic anhydride (=methylnadic anhydride), 3,4,5,6,7-hexachloro-3,6-endomethylene-$\Delta^4$-tetrahydrophthalic anhydride, succinic anhydride, adipic anhydride, trimethyladipic anhydride, azelaic anhydride, sebacic anhydride, maleic anhydride and dodecylsuccinic anhydride; and pyromellitic dianhydride, trimellitic anhydride, benzophenonetetracarboxylic dianhydride or mixtures of such anhydrides.

Novolaks, polyamines and carboxylic acid anhydrides are a preferred group of hardeners.

The composition of the invention can also contain curing accelerators and/or polymerization initiators or thermal and/or photochemical curing catalysts. Examples are: tertiary amines, salts thereof or quaternary ammonium compounds, e.g. 2,4,6-tris(dimethylaminomethyl)phenol, benzyldimethylamine, 2-ethyl-4-methylimidazole and triamylammonium phenate; or alkali metal alcoholates, e.g. sodium hexanetriolate; monophenols or polyphenols such as phenol, diomethane or salicylic acid; dicyandiamide; boron trifluoride and its complexes with organic compounds, such as BF$_3$-ether complexes and BF$_3$-amine complexes, e.g. BF$_3$-monoethylamine complex and acetoacetanilide-BF$_3$ complex; phosphoric acid; and triphenyl phosphite. Suitable photochemical curing catalysts are onium salts or metal complex salts, e.g. diazonium salts of aromatic amines, triphenylsulfonium or diphenyliodonium salts or cyclopentadienyl-iron-arene salts.

Curing accelerators and catalysts are conventionally added in an amount of 0.1–10% by weight, based on the epoxy resin. Epoxy resin hardeners are generally used in equimolar amounts, based on the epoxy groups and functional groups of a hardener.

The composition preferably contains the anthraquinone of formula I in an amount of 0.1–1, especially 0.2–0.8, mol/kg of epoxy resin, and the amine containing hydroxyl groups in an amount of 0.1–1.2, especially 0.3–1, mol/kg of epoxy resin. Additional hardeners are preferably present in an amount of 0.1–0.5, especially 0.1–0.3, mol/kg of epoxy resin.

The amines of component (d) can be aliphatic amines containing hydroxyl groups, having 2 to 30, preferably 2 to 20, C atoms and having 1 to 3, preferably 1, hydroxyl group in the aliphatic radical. The aliphatic radical can be linear or branched and interrupted by —O— or amino groups. The aliphatic radical preferably contains primary OH groups. In a preferred embodiment of the invention, the amine has the formula IV

wherein $R^5$ is H, linear or branched $C_1$–$C_{18}$-alkyl, $C_3$–$C_7$-cycloalkyl, $C_6$–$C_{10}$-aryl, $C_7$–$C_{18}$-alkaryl, $C_7$–$C_{12}$-aralkyl, $C_8$–$C_{18}$-alkaralkyl or the group —$C_yH_{2y+1-x}OH_x$, is a number from 1 to 3 and y is a number from 2 to 12, it being possible for the group $C_yH_{2y}$ to be interrupted by one or more —O— or —$NR^5$—.

$R^5$ as alkyl preferably contains 1 to 12 and especially 1 to 6 C atoms. $R^5$ as alkyl is preferably methyl or ethyl. $R^5$ is H in particular. $R^5$ as cycloalkyl preferably contains 5 or 6 ring C atoms and is e.g. cyclopentyl or cyclohexyl.

$R^5$ as aryl may be naphthyl and especially phenyl. $R^5$ as alkaryl is especially $C_7$–$C_{18}$-alkylphenyl, for example methylphenyl, ethylphenyl, dimethylphenyl, n- and i-propylphenyl, n-, i- and t-butylphenyl, pentylphenyl, hexylphenyl, octylphenyl, nonylphenyl, decylphenyl and dodecylphenyl. $R^5$ as aralkyl can be 1- or 2-phenyleth-1-yl or especially benzyl. $R^5$ as alkaralkyl is preferably alkylbenzyl having, in particular, 8 to 14 C atoms, e.g. methylbenzyl, ethylbenzyl, dimethylbenzyl, n- and i-propylbenzyl, n-, i- and t-butylbenzyl, pentylbenzyl and hexylbenzyl. If the group $C_yH_{2y}$ is interrupted by —O—, it can be an oxaalkylene radical which can have e.g. the formula —$R^6$—$(OR^7)_t$—, wherein $R^6$ and $R^7$ independently of one another are linear or branched $C_2$–$C_6$-alkylene and t is a number from 2 to 6. If the group $C_yH_{2y}$ is interrupted by —$NR^5$—, it preferably has the formula —$(R^8$—$NH)_s R^9$—, wherein $R^8$ is linear or branched $C_2$–$C_6$-alkylene, preferably ethylene, $R^9$ is linear or branched $C_1$–$C_{10}$-alkylene, preferably $C_2$–$C_6$-alkylene, and s is a number from 1 to 3. In formula IV, y is especially a number from 2 to 7.

Those amines of formula IV in which $R^5$ is H, y is a number from 2 to 7 and x is a number from 1 to 3 are a preferred subgroup.

Examples of amines of formula IV are: ethanolamine, 1-amino-2-hydroxypropane, 1-amino-3-hydroxypropane, 1-amino-4-hydroxybutane, 1-amino-5-hydroxypentane, 1-amino-6-hydroxyhexane, aminotrimethylolmethane, aminodimethylolmethane, aminomethyldimethylolmethane, aminomethyltrimethylolmethane, hydroxyethoxyethylamine, hydroxypropoxyethylamine, N-(hydroxyethyl)ethylenediamine, N-(hydroxyethyl)diethylenetriamine and $H_2N(CH_2CH_2O)_{\overline{2-6}}H$.

Primary aliphatic amines containing hydroxyl groups are epoxy resin hardeners, linear polymers being obtained when epoxy resins having 2 epoxy groups are used. The concomitant use of other hardeners gives crosslinked polymers.

When using the monofunctional anthraquinones of formula I, it is advantageous to use epoxy resins having at least 3 epoxy groups in the molecule, e.g. epoxidized novolaks, in order to obtain cross-linked epoxy resins.

The compositions of the invention are curable, the cured or cross-linked epoxy resins being photosensitive. Thin layers of metals such as copper can be deposited by electroless metal deposition on those parts of the surface which have been exposed to light.

The composition is cured in known manner, it being possible for curing to be preceded or accompanied by moulding in accordance with the conventional moulding processes, examples being the preparation of coatings on a base material by spraying, painting or knife coating, the preparation of mouldings by means of casting techniques or the preparation of composites by means of dip-coating and compression processes.

The anthraquinone of formula I can be prereacted with an epoxy resin to give adducts, which can then be cured with the amine containing hydroxyl groups and, if necessary, with a hardener.

The concomitant use of an epoxy resin hardener, especially a novolak, amine or anhydride hardener, may be advantageous. It is advisable to prereact the monofunctional anthraquinone together with the amine containing —OH and with the epoxide and then to mix the reaction product with a hardener and cure the mixture.

In addition to stepwise curing, it is also possible to mix all the components and then cure the mixture.

The components are mixed by conventional processing methods, together with a solvent if necessary. It is possible to introduce other additives conventionally used for processing or improving the properties of the cured epoxy resins, e.g. plasticizers, dyes, pigments, fillers, mould release agents or H donors. For metal deposition, metal salts or metal complexes of groups Ib or VIII of the periodic table of the elements may advantageously be present, e.g. in an amount of 0.01 to 10% by weight, based on the composition.

Curing is generally carried out at temperatures from 20° to 200° C. and especially 50° to 150° C.

The invention further relates to the cured compositions.

The cured compositions are photosensitive. The parts exposed to light appear darker than the unexposed parts. Metals can be deposited direct on the exposed parts with conventional metal deposition baths (see e.g. U.S. Pat. No. 4,510,279), especially those containing e.g. nickel or copper salts. Printed circuits, for example, can be prepared in this way. The exposed epoxy resins can also be used for optical storage.

The invention further relates to the use of a cured composition of the invention for the preparation of metallic coatings or images by electroless metal deposition after complete or partial exposure of the surface.

Exposure is preferably effected with UV light. Any desired light sources can be employed, the use of UV lamps being preferred. Examples of suitable light sources are xenon lamps, metal halide lamps and especially high-pressure and medium-pressure mercury vapour lamps.

A possible procedure for preparing the metallic coatings or images is to cure the composition of the invention, which, according to the invention, may be in the form of a layer on a base material, then to expose it over the surface or through a master and finally to treat it with a metal deposition bath.

The concomitant use of a metal salt or metal complex is superfluous. The deposited metals adhere firmly to the surface of the epoxy resin; no pretreatment is necessary. Furthermore the cured compositions have high glass transition temperatures.

The following Examples illustrate the invention in greater detail.

(A) PREPARATION EXAMPLES

EXAMPLE 1

Anthraquinone-2-carboxylic acid hydrazide

A mixture of ethyl anthraquinone-2-carboxylate (4.83 g), 25 ml of ethanol, 50 ml of dioxane and 7 ml of hydrazine hydrate is boiled under argon for 48 hours. It is poured into water and the product is isolated by filtration and dried at 60° C. in a vacuum oven. Crystallization of the crude product (4.05 g) from dimethylformamide/chloroform gives 3.01 g of product with a melting point (m.p.) of 250° C./decomposition.

Mass spectrum (indirect sample feed, 195° C.): m/e=(M+, 20%), 235 (100%).

EXAMPLE 2

(Anthraquino-2-yl)acetic acid hydrazide 14.7 g of ethyl (anthraquino-2-yl)acetate are dissolved in 500 ml of absolute ethanol, with heating. After the addition of 10 ml of hydrazine hydrate, the solution is refluxed for 20 hours. A further 10 ml of hydrazine hydrate are added and boiling is continued for 20 hours. The mixture is filtered hot and the material on the filter is washed with 50% aqueous ethanol. Crystallization of the crude product (12.5 g) from 300 ml of dimethylformamide gives 11.2 g of product with an m.p. above 300° C.

Analysis (% by weight): Calculated: C 68.57 H 4.32 N 10.00 O 17.13% Found: C 68.9 H 4.4 N 9.8 O 17.2%

EXAMPLE 3

3-(Anthraquino-2'-yl)propionic acid hydrazide (a) Diethyl (anthraquino-2-yl)malonate 48.53 g (200 mmol) of 2-chloroanthraquinone, 160.17 g (1 mol) of diethyl malonate and 500 ml of dimethyl sulfoxide (DMSO) are heated at 120° C. until everything has dissolved. The solution is then cooled to 110° C. and 165.85 g (1.2 mol) of potassium carbonate are added in portions. After stirring for 1 day at 110° C., the mixture is cooled, treated with HCl solution and extracted three times with toluene. The extracts are washed three times with water, dried over sodium sulfate and evaporated. Filtration with toluene over silica gel and recrystallization from methylene chloride/pentane yields 38.53 g (53%) of pure product with a melting point of 114°–117° C.

Elemental analysis (% by weight): Calculated: C 68.85 H 4.95 O 26.20% Found: C 68.77 H 5.14 O 25.89%

(b) Diethyl 2-(anthraquino-2'-yl)-2-carboethoxysuccinate 20.0 g (54.6 mmol) of compound (3a) are stirred with 22.63 g (164 mmol) of potassium carbonate, 18.23 g (109.2 mmol) of ethyl bromoacetate and 200 ml of DMSO for 1 hour at 25° C. The mixture is treated with toluene and dilute HCl solution. Extraction of the aqueous phase twice with toluene, washing of the toluene phases with water, drying over sodium sulfate and evaporation yields a crystalline residue which, after stirring with diethyl ether, filtration and drying, gives 19.77 g (80%) of pure product with a melting point of 80°–84° C.

Elemental analysis: (% by weight): Calculated: C 66.36 H 5.35 O 28.29% Found: C 66.65 H 5.40 O 28.54%

(c) (Anthraquino-2-yl)succinic acid 16.35 g (292 mmol) of potassium hydroxide are dissolved in 400 ml of absolute ethanol and 22.0 g (48.6 mmol) of compound (3b) are added. The mixture is stirred for 20 minutes at 25° C. and then heated to the reflux temperature over a period of 30 minutes. After cooling, it is treated with 2N aqueous HCl solution and extracted with THF/toluene (1:1). The organic phases are dried over sodium sulfate and evaporated. Stirring with diethyl ether, filtration and drying yields 15.51 g (98%) of pure product with a melting point of 245°–250° C. (decomposition).

Elemental analysis (% by weight): Calculated: C 66.67 H 3.73 O 29.60% Found: C 66.98 H 4.02 O 28.83%

(d) 3-(Anthraquino-2'-yl)propionic acid 10 g of dicarboxylic acid (c) are heated in 70 ml of quinoline for 5 hours at 140° C. under argon. The mixture is poured into 400 ml of ice water, acidified with 2N hydrochloric acid and filtered. The material on the filter is washed with water, dried (7.9 g) and recrystallized from 300 ml of glacial acetic acid. Yield: 5.3 g; m.p.: 251° C.

Elemental analysis (% by weight): Calculated: C 72.85 H 4.32 O 22.83% Found: C 72.2 H 4.3 O 23.4%

(e) Ethyl 3-(anthraquino-2'-yl)propionate 5 g of acid (3d) are refluxed in 80 ml of ethanol with 3 ml of concentrated sulfuric acid for 5 hours. The mixture is allowed to cool, the crystallized product is isolated by filtration and washed with 50% aqueous ethanol and the ester (4.3 g) is purified by crystallization from 100 ml of ethanol. Yield: 3.7 g; m.p.: 101° C.

Elemental analysis (% by weight): Calculated: C 74.02 H 5.23 O 20.76% Found: C 73.9 H 5.3 O 20.8%

(f) 3-(Anthraquino-2'-yl)propionic acid hydrazide 9.2 g of ester (e) are heated in 200 ml of ethanol with 6 ml of hydrazine hydrate for 72 hours under argon. The mixture is filtered hot and the material on the filter is washed with ethanol and 50% ethanol/water. The crude product (4.6 g) is recrystallized from 200 ml of dioxane. Yield: 3.7 g; m.p.: 229° C./decomposition.

Elemental analysis (% by weight): Calculated: C 69.38 H 4.80 N 9.52 O 16.31% Found: C 68.9 H 4.9 N 9.5 O 16.6%

EXAMPLE 4

10-(Anthraquino-2'-yl)decanoic acid hydrazide (a) Ethyl 10-phenyldecanoate

A solution of 26.15 g of 9-benzoylnonanoic acid in 260 ml of glacial acetic acid and 1 ml of 0.1N hydrochloric acid is hydrogenated (normal pressure) at 30°–35° C. with 2.6 g of palladium-on-charcoal (5% by weight) as catalyst. When no more hydrogen is taken up, the mixture is filtered and the filtrate is evaporated under reduced pressure. The residue is dissolved in 200 ml of ethanol and 2 ml of concentrated sulfuric acid and the solution is refluxed for 22 hours. The solvent is evaporated off and the residue is treated with water and extracted with ether. The organic phase is separated off, washed with water, sodium bicarbonate solution (10% by weight) and saturated sodium chloride solution, dried and evaporated. Distillation of the residue under high vacuum (1 mbar, 137°–141° C.) gives 20 g of ethyl 10-phenyldecanoate.

(b) 2-[4'-(9''-Ethoxycarbonylnonyl)benzoyl]benzoic acid

At 0°–3° C., 9.6 g of phthalic anhydride are added to a solution of 18 g of ethyl 10-phenyldecanoate in 100 ml of 1,2-dichloroethane, after which 26 g of aluminium chloride are added in portions over a period of 1 hour. After stirring for 20 hours at room temperature, the mixture is poured onto ice/2N hydrochloric acid and extracted with methylene chloride. Washing of the organic phase with saturated sodium chloride solution, drying and evaporation gives 25.1 g of 2-[4'-(9''-ethoxycarbonylnonyl)benzoyl]benzoic acid as a waxy solid which can be used for the next step without purification.

(c) 10-(Anthraquino-2'-yl)decanoic acid 12.7 g of 2-[4'-(9''-ethoxycarbonylnonyl)benzoyl]benzoic acid are added under argon to 120 ml of 10% oleum preheated to 90° C. and the mixture is stirred for 1 hour at 90° C. It is poured into 400 ml of ice water and filtered. The material on the filter is suspended with water and taken up in ethyl acetate. Drying of the organic phase, evaporation and crystallization of the residue (7.2 g) from ethyl acetate gives 4.1 g of 10-(anthraquino-2'-yl)decanoic acid with an m.p. of 135°–137° C. Mass spectrum (indirect sample feed, 210° C.): m/e=378 ($M^+$, 40%), 222 (100%).

(d) Ethyl 10-(anthraquino-2'-yl)decanoate

A solution of 4 g of 10-(anthraquino-2'-yl)decanoic acid in 80 ml of ethanol and 3 ml of concentrated sulfuric acid is refluxed for 24 hours. It is cooled to 0° C. and filtered and the product is washed with aqueous ethanol (30%). Crystallization of the material on the filter from methanol gives 3.7 g of product with an m.p. of 81° C.

Elemental analysis (% by weight): Calculated: C 76.82 H 7.44 O 15.47% Found: C 76.7 H 7.4 O 15.8%

(e) 10-(Anthraquino-2'-yl)decanoic acid hydrazide

A solution of 20 g of ester (d) in 400 ml of ethanol is refluxed for 24 hours after the addition of 10 ml of hydrazine hydrate. 15 ml of hydrazine hydrate are added and the mixture is boiled for a further 24 hours. It is filtered hot and the filtrate is concentrated by evaporation of the solvent and filtered again. Crystallization of the material on the filter (16.7 g) from 350 ml of dioxane gives 12.6 g of product with an m.p. of 190°–191° C.

Elemental analysis (% by weight): Calculated: C 73.44 H 7.19 N 7.14 O 12.23% Found: C 73.7 H 7.4 N 7.1 O 12.3%

EXAMPLE 5

10-(Anthraquino-2'-yl)decanoic acid N-1-methylhydrazide 1.26 g of 4-methylmorpholine and 1.5 g of isobutyl chloroformate are added at −15° C. under argon to a suspension of 3.8 g of 10-(anthraquino-2'-yl)decanoic acid in 40 ml of tetrahydrofuran. After stirring for 5 minutes at −15° C., the resulting solution is treated with 0.92 g of N-methylhydrazine in 10 ml of tetrahydrofuran. The mixture is stirred for 30 minutes at room temperature, the precipitated salts are filtered off, the solvent is evaporated off, the residue is taken up in 50 ml of ethyl acetate and the resulting solution is washed with 20 ml of aqueous sodium bicarbonate solution (5% by weight). The residue of the organic phase (3.3 g) is chromatographed on 500 g of silica gel with chloroform/ethyl acetate (7:1). Crystallization of the eluate (2.8 g) from toluene gives 1.03 g of product with an m.p. of 66°–67° C.

Elemental analysis (% by weight): Calculated: C 73.86 H 7.44 N 6.89 O 11.81% Found: C 74.4 H 7.5 N 6.4 O 11.4%

EXAMPLE 6

3-[(Anthraquino-2'-ylmethoxy)ethoxy]propionic acid hydrazide (a) 2-(2'-Hydroxyethoxy)methylanthraquinone A suspension of 10.14 g of 2-chloromethylanthraquinone in 50 ml of ethylene glycol is stirred for 14 hours at 160° C. It is taken up in chloroform and the resulting solution is washed with water and saturated sodium chloride solution. Crystallization of the residue of the organic phase (12 g) from toluene gives 9.0 g of 2-(2'-hydroxyethoxy)methylanthraquinone with an m.p. of 129°–130° C.

(b) Methyl 3-[(anthraquino-2'-ylmethoxy)ethoxy]propionate

A mixture of 264 mg of compound (a), 370 mg of potassium carbonate and 1 ml of methyl acrylate in 5 ml of dimethyl sulfoxide is stirred for 2 days at room temperature under argon. It is diluted with water and extracted with chloroform, the organic phase is dried and the solvents are distilled off. Chromatography of the residue on silica gel with methylene chloride/ethyl acetate (10:1) as the eluent gives 137 g of product. Mass spectrum (indirect sample feed, 190° C.): m/e=368 ($M^+$, 30%), 87 (100%).

(c) 3-[(Anthraquino-2'-ylmethoxy)ethoxy]propionic acid hydrazide

A solution of 43 mg of methyl ester (b) and 0.1 ml of hydrazine hydrate in 3 ml of ethanol is refluxed for 20 hours. It is diluted with methylene chloride and washed with water and saturated sodium chloride solution, the organic phase is dried and the solvent is evaporated off. Chromatography on silica gel with methylene chloride/ethanol (12:1) as the eluent gives 10 mg of hydrazide. Mass spectrum (indirect sample feed, 220° C.): m/e=368 ($M^+$, 10%), 221 (100%).

(B) APPLICATION EXAMPLES
EXAMPLES 7-10

11.91 g of bisphenol A diglycidyl ether and 4.95 g of 10-(anthraquino-2'-yl)decylcarboxylic acid hydrazide are heated to 180° C. under inert gas, with mechanical stirring, affording a viscous, clear yellow melt. The epoxy equivalent of the melt is 2.18 mol of epoxide/kg (determined by the method of R. R. Jay, Analytical Chemistry 36 (1964) 667).

The melt is dissolved in 40 ml of N-methylpyrrolidone and treated with 1.13 g of propan-1-ol-3-amine and 1.23 g of a phenolformaldehyde novolak with a hydroxy equivalent of 123.15 g/mol of OH. The solution is cast as a film on aluminium or a polyester base by the wire-coating technique, dried in a forced-air oven for 12 hours at 80° C. and then cured at 140° C. for 4 hours.

An analogous procedure is followed in Example 8. Examples 9 and 10 are carried out in solution, as described below for Example 9.

8.41 g of 3-(anthraquino-2'-yl)propionic acid hydrazide and 23.82 g of bisphenol A diglycidyl ether are heated to 120° C. in 50 ml of N-methylpyrrolidone under inert gas, with mechanical stirring, affording a viscous, clear yellow solution. This is allowed to cool, 2.25 g of propan-1-ol-3-amine and 1.23 g of a cresol-formaldehyde novolak with a hydroxy equivalent of 123.15 g/mol of OH are added and the mixture is stirred at room temperature. The solution is cast as a film on aluminium or a polyester base by the wire-coating technique, dried in a forced-air oven for 12 hours at 80° C. and then cured at 140° C. for 4 hours.

Table 1 shows the composition and properties of the cured resins.

The efficiency of photoreduction is determined in the following manner. A film on a polyester base with an optical density (O.D.) of 1 at 324 nm is irradiated with a high-pressure Hg vapour lamp at 40 mW/cm$^{-2}$ and the UV/VIS spectrum is run at regular intervals. The band at 324 nm decreases and the band at 386 nm increases. The ratio of the two bands after an exposure time of 2 minutes is taken as the efficiency.

PHOTOMETALLIZATION

Films on a polyester base are exposed on a thermostatically controllable vacuum heating stage at 50° C. through a negative with a high-pressure Hg vapour lamp at an intensity of 40 mW/cm$^{-2}$. This affords a dark negative image of the master, which is intensified at 45° C. in a deposition bath of the following composition (see U.S. Pat. No. 4,510,276):

| | |
|---|---|
| CuSO$_4$.5H$_2$O | 0.0665 mol/l |
| HCHO | 0.0467 mol/l |
| Quadrol | 0.0599 mol/l |
| NaOH | pH 12.6 |
| NaCN | 25 mg/l |
| 2-mercaptobenzthiazole | 10 mg/l | to give a metallic copper image.

TABLE 1

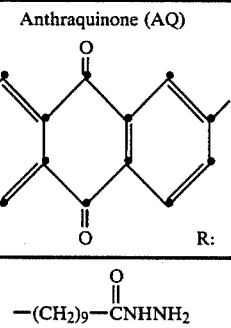

| Ex. no. | Anthraquinone (AQ) R: | AQ | 1-Aminopropan-3-ol | Bisphenol A diglycidyl ether | Novolak (equivalents) | Tg [°C.] | O.D.$_{386nm}$/O.D.$_{324nm}$ |
|---|---|---|---|---|---|---|---|
| 7 | —(CH$_2$)$_9$—CNHNH$_2$ (O) | 3 | 7 | 3 | 2 | 76 | 0.51 |
| 8 | —(CH$_2$)$_2$—CNHNH$_2$ (O) | 3 | 7 | 3 | 2 | 107 | 0.55 |
| 9 | —CH$_2$CNHNH$_2$ (O) | 3 | 7 | 3 | 2 | 102.8 | 0.62 |
| 10 | —CNHNH$_2$ (O) | 1 | 1 | 3 | — | 101 | 0.71 |

EXAMPLES 11-14

According to Example 9, the epoxy resins are prepared from 1 milliequivalent of novolak, 3 mmol of propan-2-olamine, a mixture of 1 mmol of bisphenol A diglycidyl ether "advanced" with bisphenol A (epoxy equivalent: 901 g/mol) and 6 mmol of 5,5'-dimethylhydantoin N,N'-diglycidyl ether, and 3 mmol of carboxylic acid hydrazide of the formula

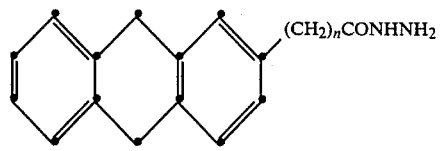

The procedure is otherwise as in Examples 7-10. The results are collated in Table 2.

TABLE 2

| Example | n | Tg (°C.) | O.D.$_{386\,nm}$/O.D.$_{324\,nm}$ |
|---|---|---|---|
| 11 | 0 | 84 | 0.40 |
| 12 | 1 | 76 | 0.52 |
| 13 | 2 | 75 | 0.61 |

TABLE 2-continued

| Example | n | Tg (°C.) | O.D.$_{386 nm}$/O.D.$_{324 nm}$ |
|---|---|---|---|
| 14 | 9 | 72 | 0.64 |

What is claimed is:

1. An anthraquinone of formula I

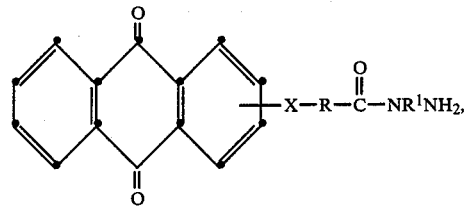
(I)

wherein X is the group —$CR^2R^3$—, where $R^2$ is H, —CN or $C_1$–$C_5$-alkyl and $R^3$ is H or —CN, $R^1$ is H or $C_1$–$C_5$-alkyl and R is a direct bond or linear or branched $C_1$–$C_{18}$-alkylene which, alone or together with the —$CR^2R^3$— group, can be interrupted by one or more —O— when $R^2$ and/or $R^3$ are not —CN.

2. An anthraquinone of formula I according to claim 1, wherein the group

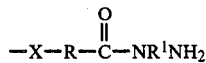

is bonded in the 2-position.

3. An anthraquinone of formula I according to claim 1, wherein X is the group —$CR^2R^3$— in which $R^2$ is H or $C_1$–$C_5$-alkyl and $R^3$ is H.

4. An anthraquinone of formula I according to claim 1, wherein $R^2$ as alkyl is methyl or ethyl.

5. An anthraquinone of formula I according to claim 3, wherein $R^2$ and $R^3$ are H.

6. An anthraquinone of formula I according to claim 1, wherein R is linear alkylene.

* * * * *